(12) United States Patent
Youngblood

(10) Patent No.: US 8,955,510 B2
(45) Date of Patent: Feb. 17, 2015

(54) DELIVERY SYSTEM FOR THERAPEUTICALLY CONDITIONED AIR

(75) Inventor: Thomas Youngblood, Midland, TX (US)

(73) Assignee: JSL Medical Products, Inc., Midland, TX (US)

( * ) Notice: Subject to any disclaimer, the term of this patent is extended or adjusted under 35 U.S.C. 154(b) by 562 days.

(21) Appl. No.: 13/344,850

(22) Filed: Jan. 6, 2012

(65) Prior Publication Data

US 2013/0174838 A1 Jul. 11, 2013

(51) Int. Cl.
```
A61F 5/08      (2006.01)
F16L 3/237     (2006.01)
A61M 16/08     (2006.01)
F16L 11/00     (2006.01)
A61M 16/06     (2006.01)
```

(52) U.S. Cl.
CPC *A61F 5/08* (2013.01); *A61M 16/06* (2013.01); *F16L 3/237* (2013.01); *A61M 16/0875* (2013.01); *F16L 11/00* (2013.01)
USPC ............ 128/200.24; 128/203.12; 128/204.18

(58) Field of Classification Search
CPC .. A47C 21/044; A47C 21/048; A47D 15/008; A61G 13/108; A61G 10/04; A61G 11/00; A61G 7/05; A61F 5/08; A61M 16/06; A61M 16/0875; F16L 3/237; F16L 11/00
USPC ................. 128/200.24, 204, 204.18, 205.26, 128/200.28, 205.12, 200.27, 201.22, 128/203.12, 203.15, 203.16, 203.25, 128/203.26, 203.27, 204.21; 138/106, 108; 601/21, 22; 5/284, 423, 93.1, 658, 724, 5/725, 726, 625.1, 652.2, 652.1; 248/49, 248/51, 74.1, 74.2, 75; 24/329, 331, 332, 24/338, 229, 339; 600/102; 604/77, 303
See application file for complete search history.

(56) References Cited

U.S. PATENT DOCUMENTS

| | | | |
|---|---|---|---|
| 4,698,890 A * | 10/1987 | Neaves | 29/412 |
| 5,336,179 A * | 8/1994 | Ryan | 604/80 |
| 5,389,037 A * | 2/1995 | Hale | 454/284 |
| 5,546,936 A * | 8/1996 | Virag et al. | 128/207.14 |
| 6,224,027 B1 | 5/2001 | Johnson et al. | |
| 6,450,166 B1 * | 9/2002 | McDonald et al. | 128/206.27 |
| 6,523,231 B1 * | 2/2003 | Lassiter | 24/339 |
| 2007/0277825 A1 | 12/2007 | Bordewick et al. | |
| 2008/0222853 A1 * | 9/2008 | Zavattieri et al. | 24/20 R |
| 2013/0220328 A1 * | 8/2013 | Jablonski | 128/205.25 |

* cited by examiner

*Primary Examiner* — Tan-Uyen (Jackie) T Ho
*Assistant Examiner* — Elliot S Ruddie
(74) *Attorney, Agent, or Firm* — Fish & Richardson P.C.

(57) ABSTRACT

An apparatus for delivery of therapeutically conditioned air to a patient may include a hollow flexible tube and at least one clamp attached to the tube. A shape retention wire may be engaged with the tube. The apparatus may be configured to direct the therapeutically conditioned air to a region near the patient's nose and mouth without being attached to the patient.

12 Claims, 4 Drawing Sheets

DELIVERY SYSTEM FOR THERAPEUTICALLY CONDITIONED AIR

BACKGROUND OF THE INVENTION

The present invention generally relates to methods and apparatus for delivering therapeutically conditioned air to a person for therapeutic purposes.

People suffering from numerous respiratory conditions may benefit from breathing humidified or nebulized misted air. Also, post-surgical patients may require such therapeutically conditioned air following post-operative intubation. This conditioned air may alleviate irritation to their respiratory system. In many cases, it is necessary to provide such therapeutically conditioned air to a patient when the patient is sleeping or recovering from anesthesia effects. Provision of such air is particularly effective if the air can be controlled to emerge from a treatment device (e.g., a nebulizer) in close proximity to a patient's nose and mouth.

Breathing masks may provide a desired focused release of therapeutically conditioned air near a patient's nose and mouth. However, such masks may be discomfiting or even frightening to a patient who may be emerging from effects of anesthesia. Such a patient may sub-consciously remove the mask and thus lose the beneficial effects of the therapeutically conditioned air.

As can be seen, there is a need for a system of providing therapeutically conditioned air in the proximity of a patient's nose and mouth while avoided the discomfiting effects of a mask applied to the patient's face.

SUMMARY OF THE INVENTION

In one aspect of the present invention, an apparatus for delivery of therapeutically conditioned air to a patient may comprise: a hollow flexible tube; at least one clamp attached to the tube; a shape retention wire engaged with the tube.

In another aspect of the present invention, a system for delivery of therapeutically conditioned air to a patient may comprise: a nebulizer; an air delivery device which includes a hollow flexible tube, at least one clamp attached to the tube and a shape retention wire engaged with the tube; and a connection tube interposed between the nebulizer and the air delivery device.

In still another aspect of the invention, and apparatus for delivery of therapeutically conditioned air to a patient prepared by a process may comprise the steps of: compressing a plurality of open-ring shaped wire supporting clips; passing a bendable shape-retention wire through a first hole in each of the clips; placing the shape retention wire and the clips inside a flexible tube; and allowing the clips to expand and engage with the tube so that, when the tube is bent into a desired configuration, the shape-retention wire maintains said configuration of the tube.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features.

Broadly, embodiments of the present invention generally provide a system for delivering therapeutically conditioned air in the vicinity of a patient's nose and mouth without attaching a delivery device to the patient.

Figure 1:
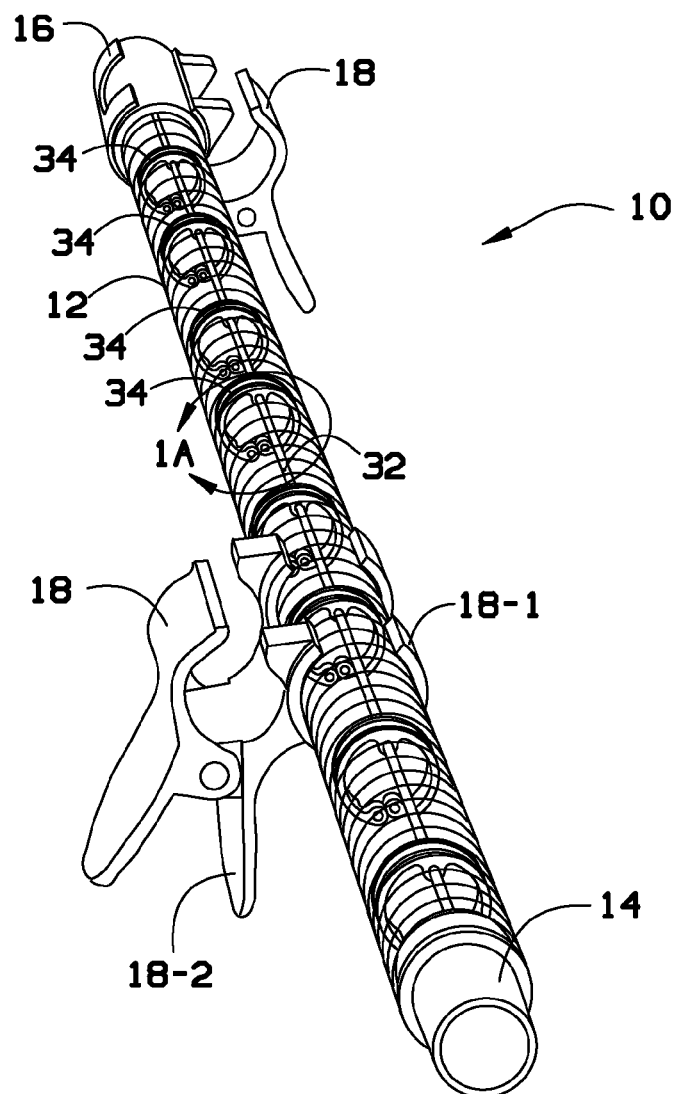
FIG. 1 is a perspective view of an air delivery device in accordance with an embodiment of the invention.

Referring now to FIG. 1, it may be seen that an exemplary embodiment of an air delivery device 10 may comprise a tube 12, an inlet member 16, an outlet member 14 and one or more clamps 18.

Figure 2:
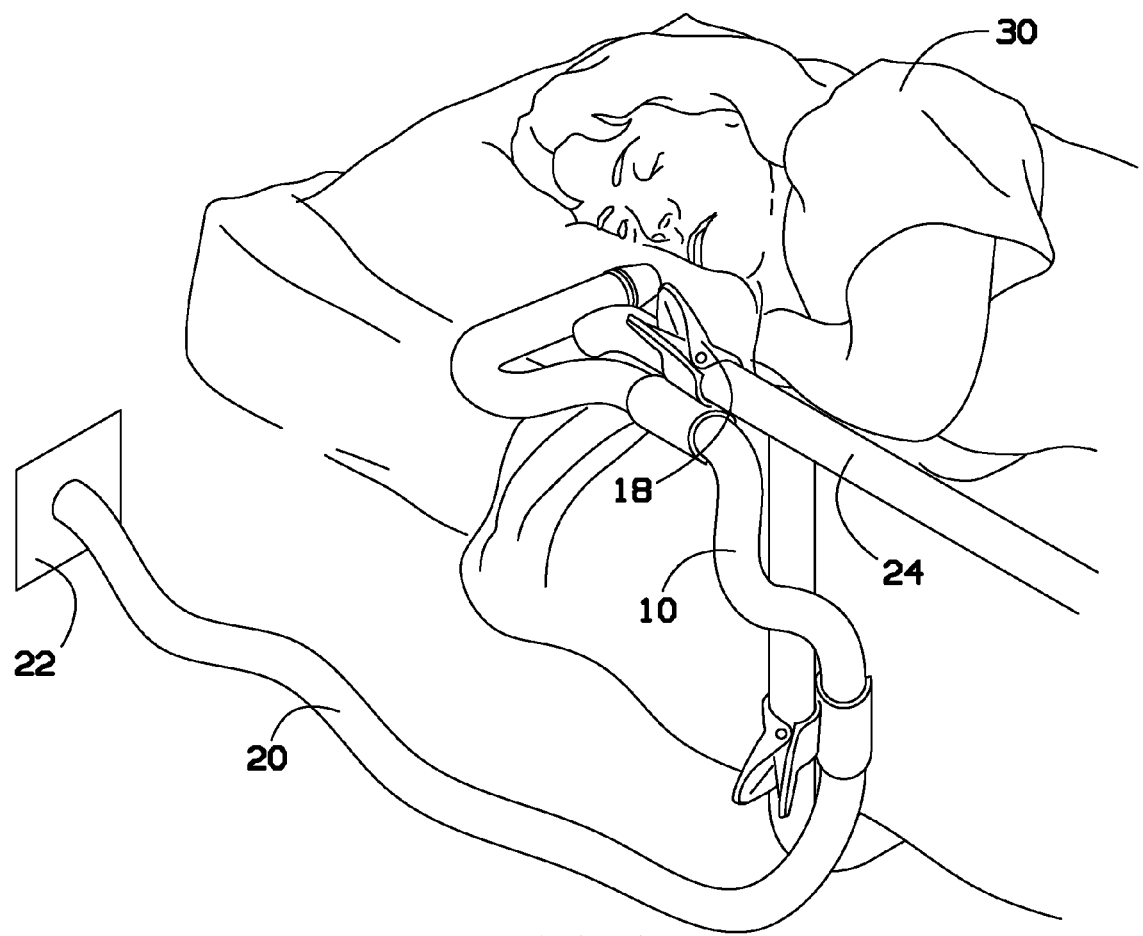
FIGS. 2 and 3 are perspective views of the device of FIG. 1 showing operational features of the device.
Figure 3:
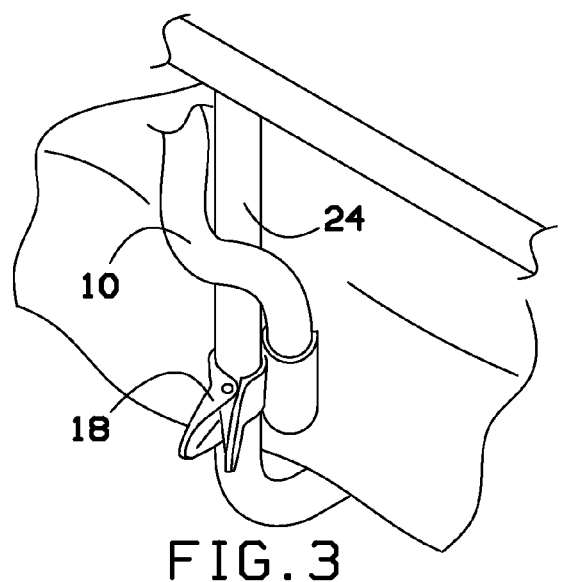

Referring now to FIGS. 2 and 3, it may be seen that, in operation, the device 10 may be connected through a connection tube 20 to a source of therapeutically conditioned air such as a centralized hospital air source 22. One of the clamps 18 may be attached to a horizontal portion of a bed rail 24. Another one of the clamps 18 may be attached to a vertical portion of the bed rail 24. It may be noted that the outlet 14 of the device 10 may be positioned next to, but not in contact with, a mouth and nose of a patient 30.

The device 10 may be provided with shape-retention elements so that the device 10 may be bent and positioned in any one of many different configurations to align with the position of the patient 30. Referring back to FIG. 1 it may be seen that a shape-retention wire 32 may be placed inside the tube 12 and supported on wire-supporting clips 34. Advantageously, the wire 32 may be soft stainless steel with a diameter between about 0.050 inch to about 0.10 inch. A plurality of the clips 34 may be spaced at approximately equal intervals along the length of the interior of the tube 12. The tube 12 may be bent into a desired configuration so that it may be attached to any supporting structure such as the bedrail 24.

Figure 4:
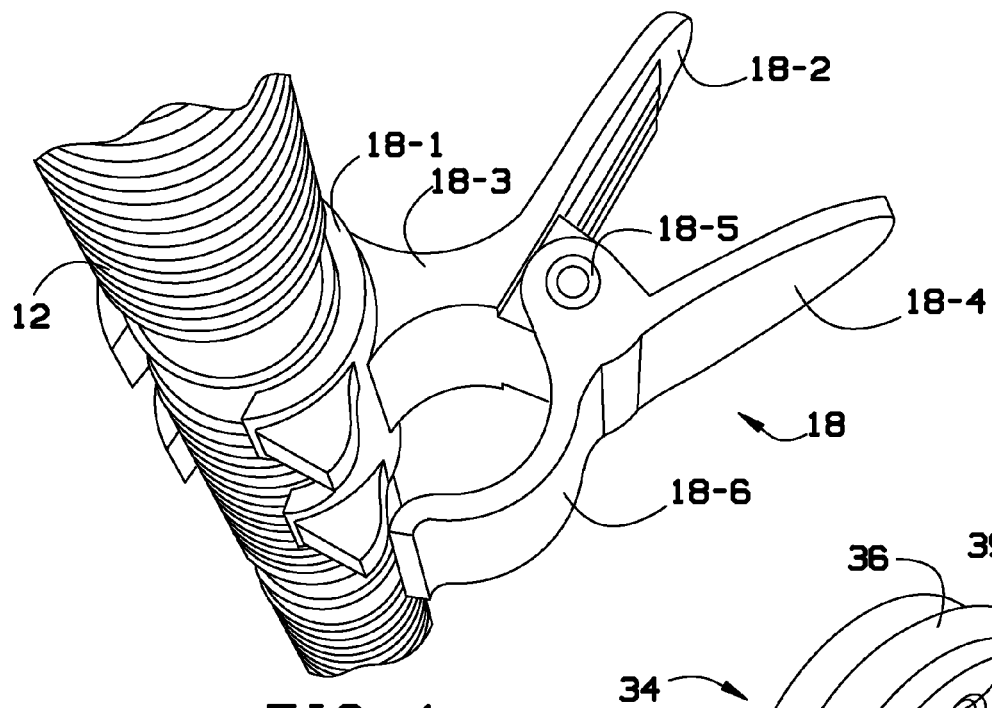
FIG. 4 is a perspective view of a clamp of the device of FIG. 1.

Referring now to FIG. 4 it may be seen that an exemplary embodiment of the clamp 18 may be spring-biased and may include a tube gripping member 18-1 which may be shaped as a partially open cylindrical structure that may be snapped onto the tube 12 at a desired location on the tube 12. A first handle member 18-2 may be integrally formed with the tube-gripping member 18-1. An arcuate connecting segment 18-3 may be interposed between the handle member 18-2 and the tube-gripping member 18-1. The arcuate connecting segment 18-3 may have a concave curved shape that may correspond approximately to a shape of the bedrail 24. A second handle member 18-4 may be affixed to the first handle member 18-2 with a torsion spring 18-5. An arcuate rail-gripping member 18-6 may be integrally formed with the handle member 18-4. The rail-gripping member 18-6 may be shaped into a concave curve that may correspond approximately to the shape of the bedrail 24.

When the two handle members 18-2 and 18-4 are pressed together, the rail-gripping member 18-6 and the arcuate segment 18-3 may separate from one another so that the clamp may be placed over the bedrail 24. When the handle members 18-2 and 18-4 are released, the torsion spring 18-5 may act to bring the rail-gripping member 18-6 and the arcuate segment 18-3 into engagement with the bedrail 24 so that the tube 12 may be held in position against the bedrail 24.

Figure 1A:
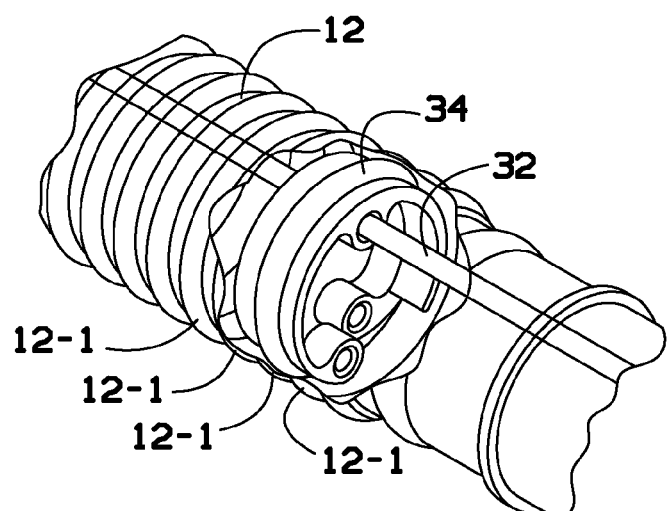
FIG. 1A is an expanded perspective view circle 1A of FIG. 1.
Figure 5:
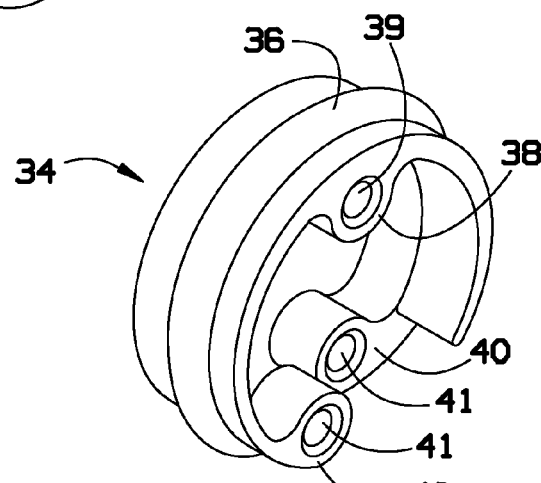
FIGS. 5 and 6 are perspective views of a wire-supporting clip of the device of FIG. 1.
Figure 6:
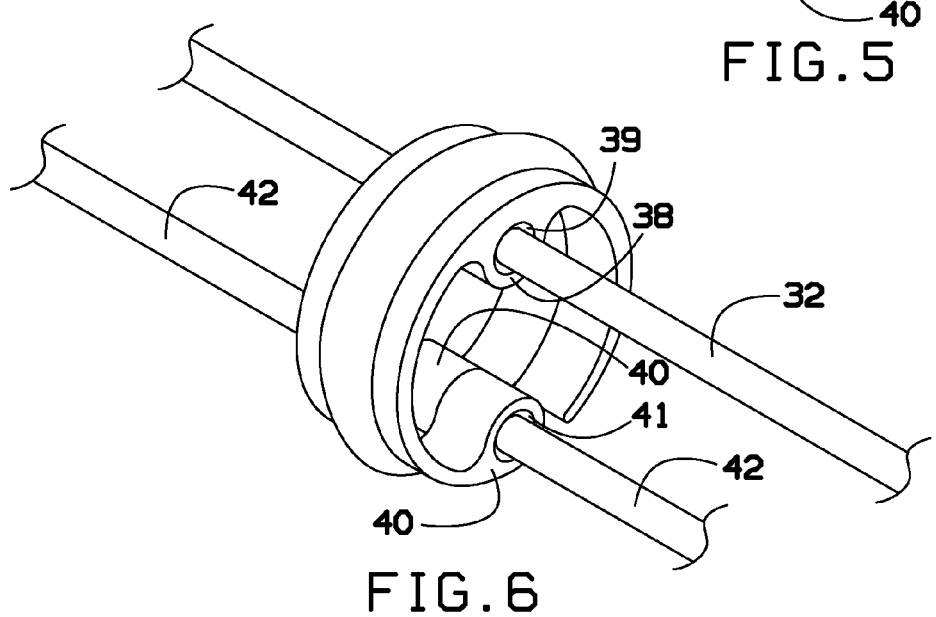

Referring now FIGS. 1A, 5 and 6 it may be seen that in an exemplary embodiment, the tube 12 may be corrugated hollow plastic air hose having an inside diameter of about 0.08 inch to about 0.10 inch. The clips 34 may be adapted to interlock with corrugations 12-1 of the tube 12 so to maintain longitudinal or axial position of the clip 34 within the tube 12.

The clip 34 may have a generally cylindrical or open-ring shape. The clip 34 may be formed from molded plastic and may be flexible. The clip 34 may be compressed so that it may have a compressed outer diameter smaller than an internal diameter of the tube 12. When released from a compressed state, the clip 34 may spring back to a nominal size with its nominal outer diameter greater than the inner diameter of the tube 12. An outer surface of the clip 34 may be provided with a retention ridge 36. The ridge 36 may be shaped to correspond to an interior shape of any one of the corrugations 12-1 of the tube 12. The clip 34 may be placed in the tube 12 in a compressed state and then allowed to expand to its nominal size. When the clip 34 is expanded within the tube 12, its longitudinal or axial position is maintained because of interlocking engagement of the ridge 36 and one of the corrugations 12-1 of the tube.

The clip 34 may have a unique configuration that may facilitate assembly of the shape-retention wire 32 into the tube 12. The clip 34 may be provided with a hollow internal projection 38 with a hole 39 through which the shape-retention wire 32 may pass. The hole 39 may have a diameter such that the wire 32 fits snugly in the hole 39. Hollow lobes 40 may be provided and positioned in two different planes so that when the clip 34 is compressed, the lobes 40 may overlap one another (see FIG. 6). When the lobes 40 are overlapped, holes 41 in the lobes 40 may be aligned so that an assembly wire 42 may be passed through both of the holes 41.

Figure 7:
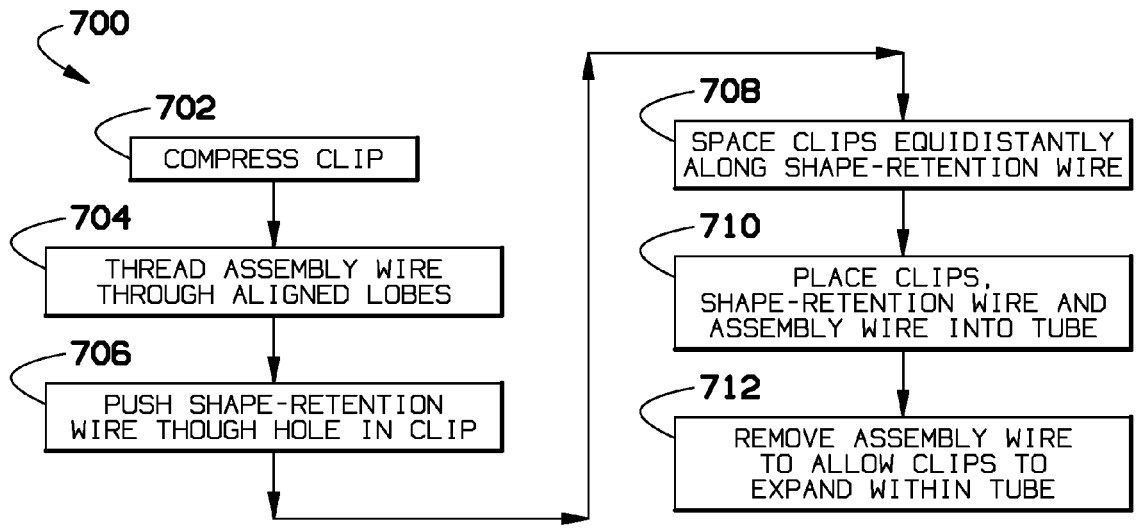
FIG. 7 is a flowchart of a method by which the device of FIG. 1 may be produced.

The shape-retention wire 32 may be installed within the tube 12 by performing the following steps shown in a flowchart 700 of FIG. 7. In a step 702, one of the clips 34 may be compressed so the holes 41 are aligned. In a step 704, the assembly wire 42 may be threaded though both of the holes 41 of one of the clips 34. In further successive steps, a plurality of the clip 34 may be similarly threaded onto the assembly wire 42. In a step 706, the shape-retention wire 32 may be pushed into the holes 39 of the clips 34 which are threaded on the assembly wire 42. In a step 708, the clips 34 may be spaced away from one another along the wire 32 so that each of the clips 34 is approximately equidistant from its adjacent clip 34. In a step 710, the equidistantly spaced clips 34, the shape-retention wire 32 and the assembly wire 42 may be inserted into the tube 12. In a step 712, the assembly wire 42 may be pulled out of the holes 41 so that the clips 34 may expand and so that the ridges 36 may engage with the corrugations 12-1. Thus the clips 34 may remain engaged with the tube 12 and the shape-retention wire 32 may be supported with the equidistantly spaced clips 34.

Figure 8:
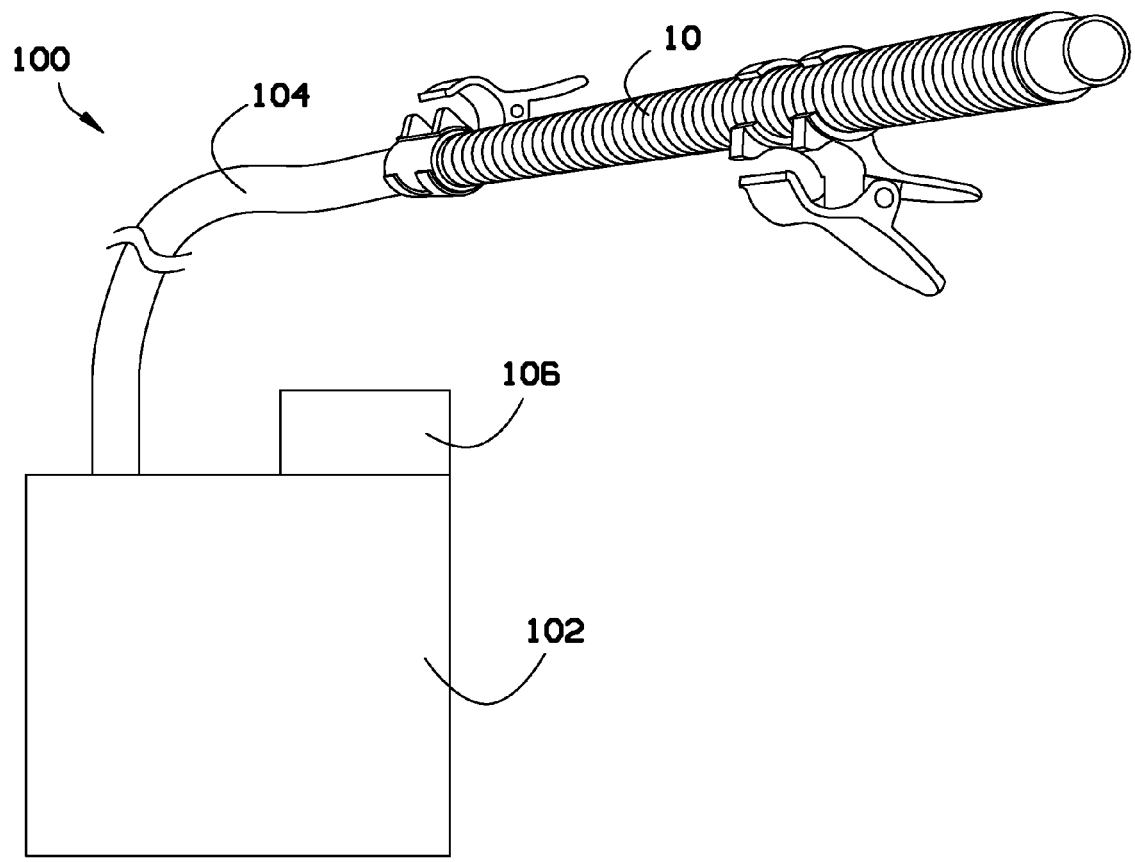
FIG. 8 is a schematic diagram of a system for delivering therapeutically treated air in accordance with an embodiment of the invention.

Referring now to FIG. 8, it may be seen that an exemplary standalone air delivery system 100 may be constructed and may be useful in a residential setting in which a patient may be in his or her own bed at home. The system 100 may comprise a nebulizer 102, a connection hose 104 and one of the air delivery devices 10. Optionally, the system 100 may include a medication dispensing device 106 which may be employed to inject medication into an air stream that may be conveyed to a patient though the air delivery device 10.

It should be understood, of course, that the foregoing relates to exemplary embodiments of the invention and that modifications may be made without departing from the spirit and scope of the invention as set forth in the following claims.

What is claimed is:

1. An apparatus for delivery of therapeutically conditioned air to a patient comprising:
   a hollow flexible tube;
   at least one clamp attached to the tube;
   a shape-retention wire engaged with the tube; and
   a plurality of wire supporting clips positioned inside the tube and engaged with the shape-retention wire, wherein the clips include hollow lobes positioned on two different planes so that when the clips are compressed the lobes overlap one another.

2. The apparatus of claim 1 wherein the shape-retention wire is positioned inside the tube.

3. The apparatus of claim 1 wherein the shape-retention wire is soft stainless steel with a diameter between about 0.050 inch to about 0.10 inch.

4. The apparatus of claim 1 wherein the tube is corrugated and the clips are provided with ridges that are engaged with corrugations of the tube.

5. The apparatus of claim 1 wherein the clips have a compressible open-ring configuration with a compressed outer diameter smaller than an inner diameter of the tube and with an uncompressed nominal outer diameter greater than the inner diameter of the tube.

6. The apparatus of claim 1 wherein the hollow lobes have holes that are aligned with one another when the lobes are overlapped with one another.

7. The apparatus of claim 1 wherein at least one clamp includes:
   an open cylindrical tube gripping member configured to be snapped onto the tube at a desired location on the tube, the tube gripping member having an arcuate rail-gripping segment; and
   an arcuate rail-gripping member attached to the tube gripping member and spring biased to apply clamping pressure against the tube gripping member.

8. The apparatus of claim 7 comprising at least two of the clamps.

9. A system for delivery of therapeutically conditioned air to a patient comprising:
   a nebulizer;
   an air delivery device which includes a hollow flexible tube, at least one clamp attached to the tube, a shape-retention wire engaged with the tube, and a plurality of wire supporting clips positioned inside the tube and engaged with the shape-retention wire, wherein the clips include hollow lobes positioned on two different planes so that when the clips are compressed the lobes overlap one another; and
   a connection tube interposed between the nebulizer and the air delivery device.

10. The system of claim 9 further comprising a medication dispensing device configured to inject medication into an airstream that passes through the air delivery device.

11. An apparatus for delivery of therapeutically conditioned air to a patient prepared by a process comprising the steps of:
   compressing a plurality of open-ring shaped wire supporting clips;

passing a bendable shape-retention wire through a first hole in each of the clips;

placing the shape retention wire and the clips inside a flexible tube;

allowing the clips to expand and engage with the tube so that when the tube is bent into a desired configuration, the shape-retention wire maintains said configuration of the tube;

overlapping two hollow lobes of each of the clips during the compressing step so that holes in the lobes are aligned with one another;

passing an assembly wire through the aligned holes of the lobes of all of the clips so that the assembly wire secures the clips in a compressed state;

inserting the assembly wire into the tube along with the clips and the shape-retention wire; and removing the assembly wire from the clips after the clips are in position in the tube so that the clips expand and engage with the tube.

12. The apparatus of claim 11 wherein the process further comprises positioning the clips axially along the shape-retention wire so that the clips are substantially equidistant from one another.

\* \* \* \* \*